(12) United States Patent
Hilscher et al.

(10) Patent No.: US 11,549,928 B2
(45) Date of Patent: Jan. 10, 2023

(54) DEVICE AND METHOD FOR CRUMBLING ROOT CROPS AND FOR DETERMINING COMPONENTS IN ROOT CROPS

(71) Applicant: KWS SAAT SE & CO. KGAA, Einbeck (DE)

(72) Inventors: Elke Hilscher, Einbeck (DE); Frank Friedhoff, Einbeck (DE)

(73) Assignee: KWS SAAT SE & CO. KGAA, Einbeck (DE)

( * ) Notice: Subject to any disclaimer, the term of this patent is extended or adjusted under 35 U.S.C. 154(b) by 0 days.

(21) Appl. No.: 17/689,535

(22) Filed: Mar. 8, 2022

(65) Prior Publication Data
US 2022/0187268 A1 Jun. 16, 2022

Related U.S. Application Data

(63) Continuation of application No. 17/104,174, filed on Nov. 25, 2020, now Pat. No. 11,307,188, which is a continuation of application No. 15/288,384, filed on Oct. 7, 2016, now Pat. No. 10,877,014.

(51) Int. Cl.
*G01N 33/02* (2006.01)
(52) U.S. Cl.
CPC .................. *G01N 33/025* (2013.01)
(58) Field of Classification Search
CPC .............. G01N 33/025; G01N 21/85
USPC ......................... 241/24.26; 436/47
See application file for complete search history.

(56) References Cited

U.S. PATENT DOCUMENTS

| | | | |
|---|---|---|---|
| 2,403,910 A | 7/1946 | Christansen |
| 2,559,551 A | 7/1951 | Weber |
| 2,583,885 A | 1/1952 | Russenberger |
| 3,726,208 A | 4/1973 | Brengman |
| 6,998,559 B2 | 2/2006 | De Baerdemaeker et al. |
| 7,024,942 B1 | 4/2006 | Jackson et al. |
| 7,223,431 B2 | 5/2007 | Owens |
| 10,051,787 B2 | 8/2018 | Todd et al. |
| 2010/0121484 A1 | 5/2010 | Blanc et al. |
| 2010/0216114 A1 | 8/2010 | Friedhoff |

FOREIGN PATENT DOCUMENTS

| | | |
|---|---|---|
| DE | 26 11 636 B1 | 3/1977 |
| DE | 3313928 A1 | 10/1984 |
| DE | 9011121 U1 | 11/1991 |
| GB | 2056880 A | 3/1981 |
| WO | 1999/058959 A1 | 11/1999 |

OTHER PUBLICATIONS

Extended European Search Report Issued EP16192765.2 dated Mar. 21, 2017, 7 pages.

*Primary Examiner* — Omar Flores Sanchez
(74) *Attorney, Agent, or Firm* — Troutman Pepper Hamilton Sanders LLP

(57) ABSTRACT

The invention relates to a device for crumbling root crops into substantially equal sized pieces, comprising: a main frame having an inlet side and an outlet side; a root crop supply at the inlet side; at least one crumbling shaft rotatable supported in the main frame, the crumbling shaft being provided with a plurality of curved hooks, which are curved into a direction of rotation of the crumbling shaft; and a non-rotating cutting rake having a plurality of protrusions and recesses and forming a counter blade for the hooks, wherein the hooks are arranged for interlaced movement with said recesses of the non-rotating rake. The invention moreover concerns a system and a corresponding method.

20 Claims, 10 Drawing Sheets

FIG. 10
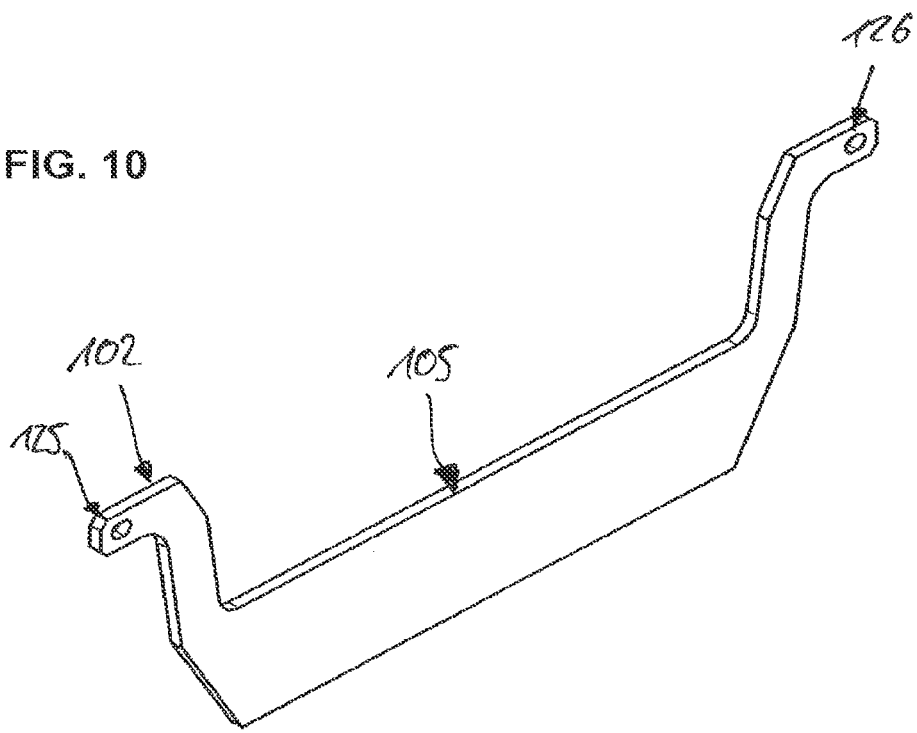
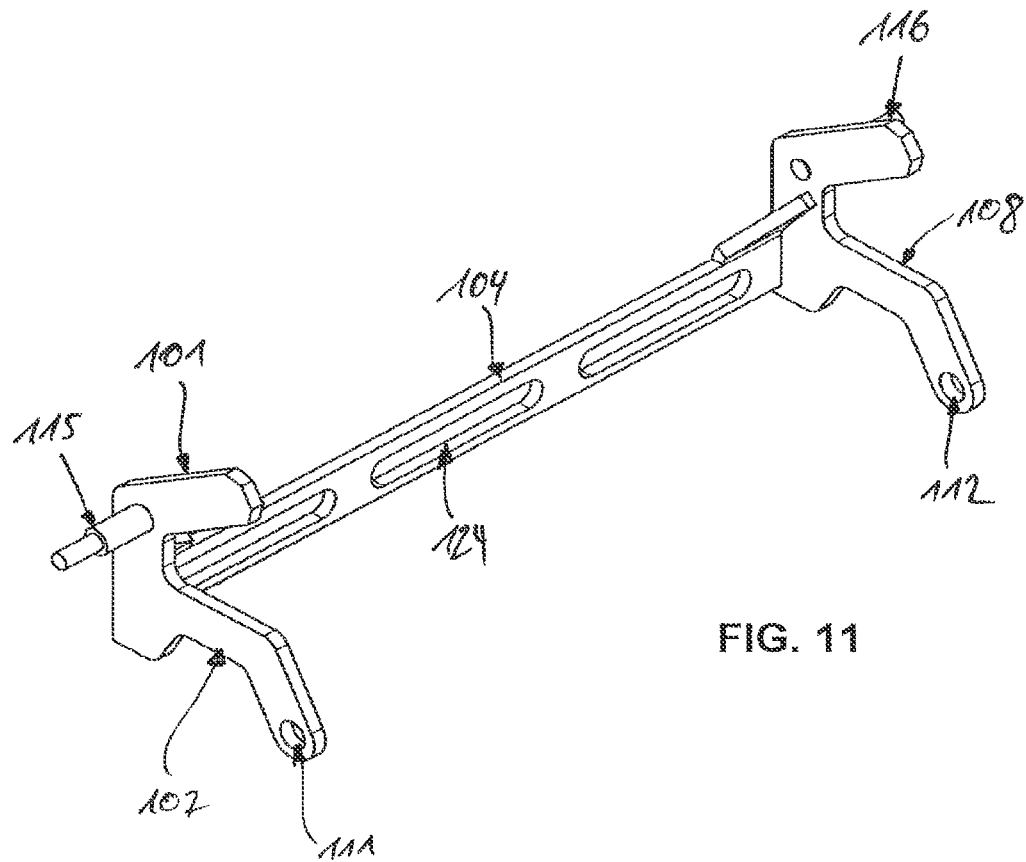
FIG. 11

DEVICE AND METHOD FOR CRUMBLING ROOT CROPS AND FOR DETERMINING COMPONENTS IN ROOT CROPS

CROSS-REFERENCE TO RELATED APPLICATIONS

This application is a continuation of U.S. application Ser. No. 17/104,174, filed Nov. 25, 2020, which is a continuation of U.S. application Ser. No. 15/288,384, filed on Oct. 7, 2016. The entire contents of these applications are incorporated herein by reference in their entirety.

TECHNICAL FIELD

The present invention relates to a device for crumbling root crops into substantially equal sized pieces, a device for determining components in root crops and a corresponding method.

BACKGROUND

In the cultivation of root crops, measurement of contents plays an important role. Root crops, for the purposes of this patent application, are root crops such as sugar beets, fodder beet, red beet, and turnips, as well as tubers such as potatoes, yam and Jerusalem artichokes. Cultivation involves a continuous, systematic selection of suitable root crops with respect to, for example, biomass yield, ingredients or disease tolerance. To be able to exercise such a selection, the contents of these crops are regularly analyzed. This is associated with a high investment in terms of labor and expense. Ultimately, however, the success of a breeding program is contingent upon the rapid and reliable analysis of the contents of root crops.

For culturing and trail purposes, root crops are grown in the field in so-called "plots". A plot represents a parcel of land of pre-measured size, and permits the cultivation of several crops, their number providing a statistical indication regarding the nature and distribution of crop yield. In the production of sugar beets one finds in general about 90 beets per plot. The plot is rated for productive capacity for sugar beets, and, after uprooting, the sugar beet is analyzed for content. Such an analysis takes place by means of conventional series techniques, which provide high accuracy. The goal however is to keep the cost of analysis to a minimum.

Structure and composition of the sample used for analysis are crucial for the accuracy of determining of the content. It should be in particular be taken into consideration that, due to genetic, crop cultivation, and above-all environment-contingent influences on growth, significant differences occur from plant to plant in the concentrations of quality-determining ingredients. Furthermore, a non-uniform distribution of concentration of the relevant constituents also is found within individual root crops such as beets and in the bodies or potato tubers. This heterogeneity of the object of analysis has led to high sampling requirements, which was solved for beets, turnips and potatoes so far by the generation of so-called mash samples. Although the procedures have been continuously improved over time with respect to analysis of, for example, beet pulp (DE 26 11 636 B1) and potato mash (Ziolko and Jehle (2002), GIT Laboratory Journal 2000, 268-273) these mash-samples, since they represent only a sampling of the total population of the crops of a plot, are only limitedly representative. As a result of such non-representative sampling, significant distortions may occur in the measurement of ingredients.

Automated laboratories are known, in which ingredients are determined in a serial manner following extraction of pulp samples with aluminum sulfate or lead acetate. In addition, near-infrared spectroscopy (NIRS) has proven to be useful in the analysis of ingredients from crops tested in analytical laboratories, which is carried out for mashed raw potato samples, samples of potato pulp, beet pulp samples, technical juices and special byproducts of sugar production from beets (Haase (2006), Starch-Starke Vol 58 (6), 268-273; Heppner et al. (2000), Sugar Industry, 125 No. 5, 325-330; Fernandez et al. (2008), Journal of Near Infrared Spectroscopy 16, 105-110). This spectroscopic method makes it possible to determine several analytes simultaneously in a sample, provides a quick availability of results and avoids the use of reagents; it thus reduces the cost and time of an analysis.

The use of NIRS as an analytical measurement method for the determination of ingredients in root crops has so far been restricted to the laboratory environment and therefore has the disadvantage that in addition to the actual analysis, a number of other preparatory sample treatment steps are needed, including activities such as fall harvesting, cleaning, collecting, storage, packing, labeling, freezing and sending of samples to the investigating laboratory. This increases the cost and the time required for analysis as a whole.

For cereals, maize and grass, NIR spectroscopy has already been used for real-time analysis of substances in conjunction with harvesting machines (WO 99/58959 A1). Here, a near infrared (NIR) probe composed of directed light source and sensor is oriented towards the flow of harvested materials, which consists of cereal grains, or even harvested chopped corn or grass chaff.

In practice, however, it has been found that a lack of controllability over the chopped materials with this method a separation can already begin to take place prior to the analysis, as a result of which distortions of the analytical results have occurred. Besides this, the known harvesting machines are not suited for analysis of root crops of individual parcels.

Moreover, from US 2010/0216114 A1, a process having the following steps is known: finely dividing the root crops of a plot into substantially equal sized fine pieces, generating a stream of fine pieces of root crop and transporting the fine pieces of root crop with the aid of a transport device, homogenizing or making uniform the stream of fine pieces of a root crop, irradiating the stream of fine pieces of a root crop with light of the near infrared range, recording the reflected radiation, converting radiation into a spectral signal, processing of the spectral signal for determination of the components. In the same document, also a device for performing the process is disclosed, the device comprising a apparatus for reducing the root crop to fine pieces, a transport device, a device to equalize a stream of reduced root crops and a measuring device for identification and quantification of ingredients.

Even though the apparatus for reducing the root crop to fine pieces is effective, it has shown that particular reduction and the structure of the root crop pieces is essential for a subsequent analysis using the NIRS-method. It is essential that the root crop pieces are substantially equal sized, not too large and not too small, and relatively dry. It has been found by the inventors of the present invention that mashed root crops are difficult to analyze, and the same is true for too big pieces of cut root crops. Therefore, improvement of the already known apparatus is needed.

SUMMARY

According to an embodiment of the invention, a device for crumbling root crops into substantially equally sized pieces comprises: a main frame having an inlet side and an outlet side; a root crop supply at the inlet side; at least one crumbling shaft rotatable supported in the main frame, the crumbling shaft being provided with a plurality of curved hooks, preferably curved into a direction of rotation of the crumbling shaft; and a non-rotating cutting rake having a plurality of recesses and preferably protrusions and forming a counterblade for the hooks, wherein the hooks are arranged for interlaced movement with said recesses of the non-rotating rake. The hooks are curved and may have a small axial size compared to the axial length of the respective crumbling shaft. The rake also has a sealing function and ensures that only pieces with a sufficiently reduced size may pass to the outlet side. The hooks are adapted to crumble pieces of the root crop rather than cutting it. They break pieces off root crops out of the whole fruit and therefore the pieces are rather dry and do not comprise a flat and wet cutting surface. To support this function, the hooks may comprise a blade portion at the tip.

According to another embodiment, the cutting rake is adjustable in height for adjusting a vertical distance to said crumbling shaft. When the distance between the cutting rake and the crumbling shaft is increased, the crumbled pieces of root crop tend to be larger, while a reduced distance leads to smaller pieces of crumbled root crops. Also, the rotational speed of the crumbling shaft may be adjusted for achieving such an effect. In one embodiment, the crumbling shaft is connected to a drive for driving the crumbling shaft, in particular a motor drive. Normally, the crumbling shaft rotates in the range of 300 to 1000 rpm, while a higher rotational speed leads to reduced piece sizes, and vice versa.

In yet another embodiment, the device comprises a cleaning rake adjacent to or opposite the cutting rake for stripping off root crop pieces from the hooks. When the hooks are rotating upwards again, it is desirable that pieces, which are pierced by the hooks, or adhering to the hooks, are stripped off. Moreover, such a cleaning rake also has a sealing effect, such that pieces, which are larger than the recesses between protrusions of the rake, are not able to pass to the outlet.

According to another embodiment of the present invention, the device comprises a de-clogging device for de-clogging clogged root crops from the rake. It may happen that a root crop sticks in the device and is not crumbled anymore, since it may be located at a position where the hooks cannot reach it, or the hooks are blocked by the root crop. It may also happen that the root crop is cut at one place by the hooks and the hooks only move through the root crop, which does not move anymore, and thus do not crumble off additional pieces. The de-clogging device is operable for de-clogging such root crops and may incorporate one or more elements, e.g. bars, which are movable upwards or any other direction for moving the clogged root crops for bringing them again into a position engageable with the hooks.

According to a further embodiment of the present invention, the device may comprise a set of first and second crumbling shafts supported in said frame, wherein the first and second crumbling shafts are arranged for a counter rotating, wherein one rake is provided between the crumbling shafts having opposingly arranged protrusions and recesses. The rake, which is positioned between these shafts, is the cutting rake. Additionally, two cleaning rakes are preferably arranged at opposite sides distal from the cutting rake.

In yet another embodiment, two sets of such sets of first and second crumbling shafts are arranged side by side, in a parallel manner, such that at least four crumbling shafts are provided in one device.

According to another embodiment of the present invention, a device for determining components in root crops comprises: a device for crumbling root crops into substantially equal sized pieces, the device for crumbling root crops comprises a main frame having an inlet side and an outlet side; a root crop supply at the inlet side; at least one crumbling shaft rotatable supported in the main frame, the crumbling shaft being provided with a plurality of curved hooks, preferably curved into a direction of rotation of the crumbling shaft; and a non-rotating cutting rake having a plurality of recesses and preferably protrusions and forming a counterblade for the hooks, wherein the hooks are arranged for interlaced movement with said recesses of the non-rotating rake; the device for determining components in root crops further comprises: a transport device for transporting the stream of root crop crumbles; an equalizing roller for homogenizing the stream of root crop crumbles; and a measuring device for identification and quantification of ingredients.

In yet another embodiment of the present invention, a method for determining components in root crops, comprises the following steps, in this sequence: crumbling the root crops into substantially equal sized fine pieces using a device for crumbling root crops into substantially equal sized pieces, generating a stream of fine pieces of root crop, and transporting the fine pieces of root crop with the aid of a transporting device; homogenizing or evenly distributing the fine pieces of root crop in the stream; irradiating the stream of fine pieces of root crop with a light of the near infrared range; recording the reflected and/or absorbed radiation; converting radiation into a spectral signal; and processing of the spectral signal for determination of the components; wherein the device for crumbling root crops into substantially equal sized pieces comprises: a main frame having an inlet side and an outlet side; a root crop supply at the inlet side; at least one crumbling shaft rotatable supported in the main frame, the crumbling shaft being provided with a plurality of curved hooks, preferably curved into a direction of a rotation of the crumbling shaft; and a non-rotating cutting rake having a plurality of recesses and preferably protrusions and forming a counterblade for the hooks, wherein the hooks are arranged for interlaced movement with said recesses of the non-rotating rake.

BRIEF DESCRIPTION OF THE DRAWINGS

Embodiments of the present invention will be detailed subsequently, referring to the appended drawings, in which:

FIG. 10 is a perspective view of a first de-clogging element;

FIG. 11 is a perspective view of a second de-clogging element; and

DETAILED DESCRIPTION

Figure 1:
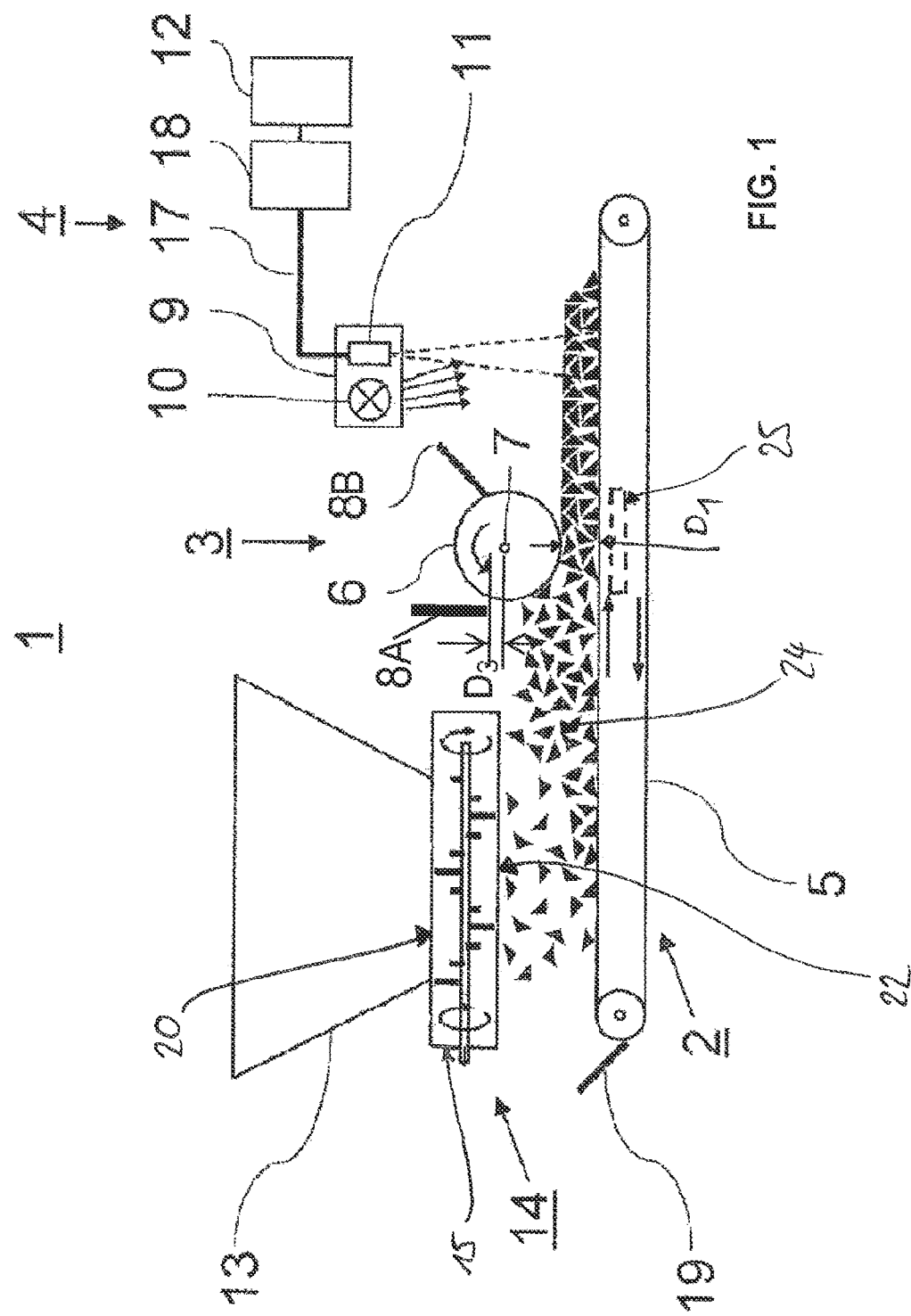
FIG. 1 is a schematic drawing of a device for determining components in root crops.

In FIG. 1, a device 1 for determining components in root crops is shown schematically: cleaned root crops of a parcel are collected in a funnel-shaped hopper 13. From the hopper 13, the root crops move to a device 14 for crumbling root crops into substantially equal sized pieces, as it will be described in detail below. In the device 14, the root crops are reduced into essentially even sized pieces. The device 14 comprises a main frame 15 having an inlet side 20 and an outlet side 22. The root crop pieces 24 fall onto an apparatus for transportation 2, for example a conveyer belt 5, and accumulate there. The speed of the conveyer belt 5 is adjustable and is adapted to the speed at which the root crops are reduced, however, the accumulation of pieces from the device 14 on the conveyer belt 5 does not result in a smooth surface. On the conveyer belt 5, the accumulated root crop pieces 24 therefore go into a device 3, which provides a comparative even distribution of the sample flow. The device 3 has a roller 6 in the form of an elongate shaft, which is arranged at a constant and fixed distance $D_1$ above the conveyer belt 5 along the roll axis 7. Using this roller 6, the sample stream of crumbled root crops 24 is compressed to a certain thickness, whereby a smooth surface results. The distance between the roller 6 and conveyer belt 5 is adjustable; it is preferably between 100 mm and 150 mm.

A motor drives the roller 6 and rotates it in the running direction of conveyer belt 5, as indicated by the arrow. The motor may be driven electrically, hydraulically, or pneumatically. In a preferred embodiment the movement of the roller 6 is coupled with drive of the conveyer belt 5.

As the crumbled root crops 24 contact the roller 6, they are spread on the conveyer belt 5 and are subject to a compressive force as a function of the distance between the roller 6 and the conveyer belt 5. The so compressed sample of root crops 24 thus has imparted to it a smooth surface and a constant height.

In embodiments of the invention the roller preferably comprises a smooth surface, as e.g. a polymer surface or a steel surface. The polymer surface might be provided as a polymer layer on a frame structure of the roller 6, or the whole, substantially the complete roller 6, might be formed of a polymer. It has shown that a smooth surface is beneficial for homogenizing the stream. Moreover, it is preferred that the surface has low adhesive features, as e.g. a non-stick surface or a non-stick coating. In alternative embodiments, also additional rollers might be provided, which has shown to be beneficial, when the stream of root crop pieces 24 is large.

Below the belt 5, a block 25 can be provided, for providing a counterpart for the pressure of the roller 6. Block 25 ensures that the belt 5 is not pushed downwards with respect to FIG. 1 and thus, the stream of crumbled root crops 24 substantially has a height of $D_1$ after passing the roller 6.

In one embodiment of the invention scrapers 8A, 8B, 19 are provided on the roller 6 and/or the conveyer belt 5 and continuously clean the roller surface and belt 5 during operation, thus avoiding the cross-mixing of two root crop samples of consecutive processed plots.

Moreover, a clumping or accumulation of root crop sample 24 on the conveyer belt 5 and roller 6 can be ruled out, which would otherwise severely disturb the comparative homogenization of the sample flow. Preferably, the scraper is a wiper 8A positioned directly in front of the roller 6 relative to the direction of movement of the conveyer belt 5. Particularly preferred the wiper 8A is cleaning the roller surface above the rotation axis of the roller, i.e. the wiper 8A is positioned or affects the roller surface above the rotation axis 7 of the roller. For processing of beets the optimum distance between rotation axis of the roller and wiper 8A ($D_3$) is around 20 mm.

Directly downstream of the roller 6 is an apparatus determining components in root crops 4 (for example NIR- or THz-spectrometer) using e.g. a sensor head 9 with a light source 10 and a sensor 11 for detecting the radiation reflected or absorbed from the smooth surface of the stream of root crop sample 24 in the wavelength range from 850 nm to 1650 nm. The sensor head 9 is elevated at a fixed distance of 200 mm to 250 mm of the surface of the smooth sample flow 24 and can be pivoted as desired relative to the sample stream 24, e.g. in the direction of the conveyer belt parallel or at a 90 degree angle. In this way, it is possible for instance to sense and record the entire width of the sample stream 24.

The sensor 11 continuously records reflected or absorbed radiation and transmits it via optical fiber 17 to a spectrometer 18, which converts the spectrally resolved radiation wavelengths into digitized portions, at regular intervals of 40 ms. Thus, during the flow-by of the stream of root crop samples, several hundred such spectra are produced, which are filtered and averaged by a processor 12. By comparison with suitable calibration data, the identities and concentrations of quality-ingredients such as sugar, starch, crude protein, crude ash, crude fiber content, crude fat, anions or cations, NDF (neutral detergent fibre), ADF (acid detergent fibre), (acid detergent lignin), Hemicellulose (HCEL) or Cellulose (CEL) are determined with high precision and are output.

It has shown in the past that it is important to achieve a substantially homogeneous flow of crumbled root crops 24, with same sized pieces and without excess liquid draining from the pieces. The liquid tends to reflect the light, which makes the determination of components of the root crops more difficult. Tests have been carried out with a root crop mill, which is usually used to chop root crops for animal feed production. However, these devices have been shown to be of too less strength for crumbling a stream of a whole parcel and also might result in uneven pieces. Also, a shredding machine has been tested; however, the result was poor, since the pieces of root crops where very uneven and had a high spread in piece size. Further tests have been carried out with a root crop saw and a mill and the root crops have been reduced to a normal mash, a coarse mash, juice, large pieces (e.g. 15-20 $cm^3$), small pieces (3-8 $cm^3$) and slices of ca. 500-800 $cm^3$. When either using the mash, the normal mash or the coarse mash, it has shown that the results are not exact, which may be a result of the fast degradation of the material. When using fine pieces, the problem is that a small water film emerges on the pieces and this is corrupting the NIRS or THz spectroscopy measurement, since the water film cannot be passed by the radiation. Slices of root crops had the negative effect that their distance between the stream on the conveyer belt and the sensor head varies, when the slices are put upon each other or in case they are not completely evenly cut. Therefore, it is important to achieve an even and homogeneous particulate stream, which is relatively dry, has even root crop piece sizes and a relatively flat surface.

Providing such a stream of crumbled root crops can be achieved by means of the device 14 for crumbling root crops according to the present invention.

Figure 2:
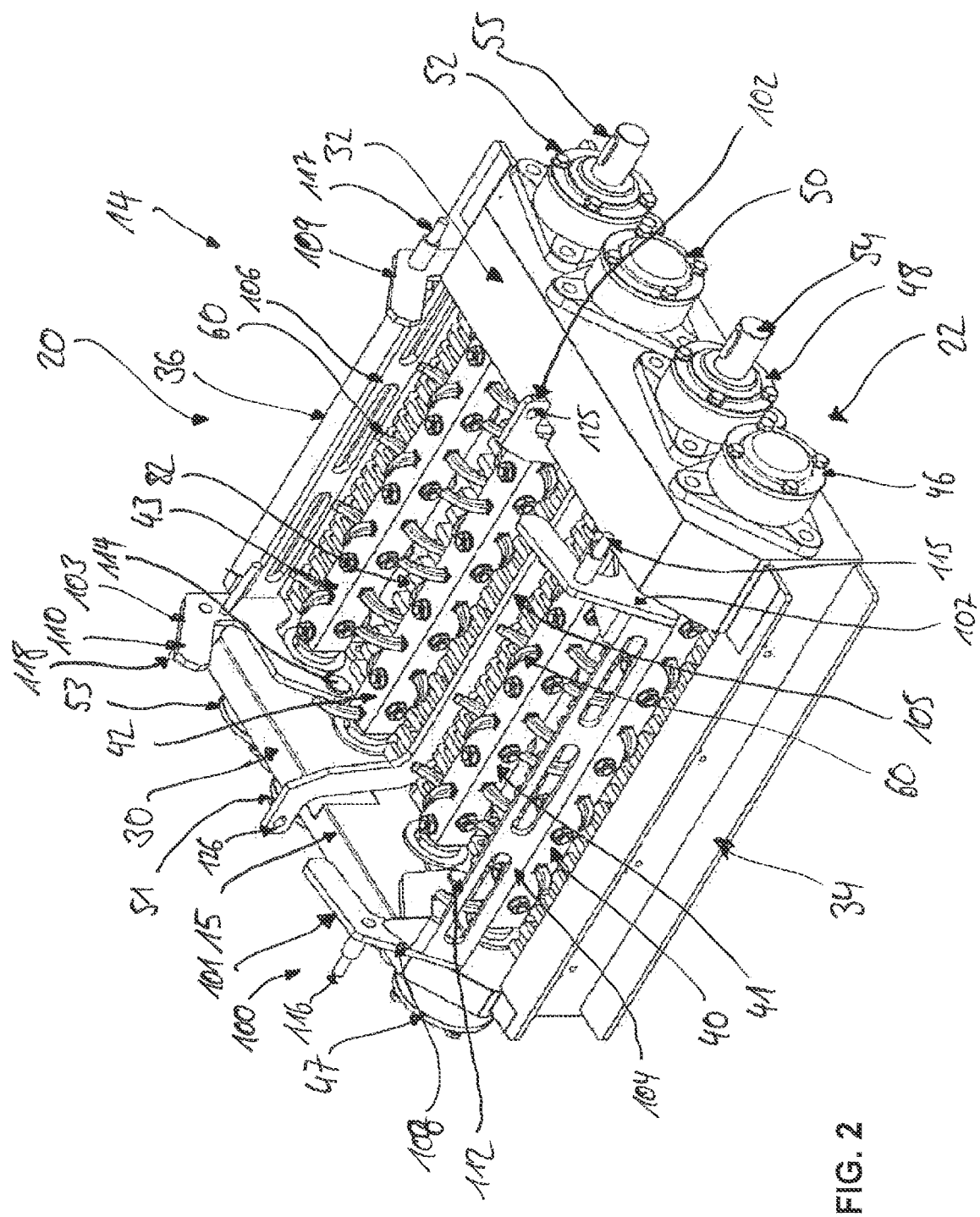
FIG. 2 is a perspective view of a device for crumbling root crops.

The device 14 for crumbling root crops into substantially even equal sized pieces in a first perspective view is shown in FIG. 2. The device comprises a frame 15, which is substantially rectangular and comprises first and second head portions 30, 32, which are opposingly arranged and first and second side portions 34, 36, which are also opposingly arranged. All side portions 30, 32, 34, 36 are arranged in a rectangular angle to each other, such that a frame is build. At the inlet side 20, normally a hopper 13 would be placed, which is not shown in FIG. 2 for simplicity (see FIG. 1).

Within the main frame 15, according to this particularly preferred embodiment, four crumbling shafts 40, 41, 42, 43 are rotatable supported. The crumbling shafts 40, 41, 42, 43 will be described in more detail with reference to FIG. 6 below.

Axial ends 44, 45 (see FIG. 6) of the crumbling shafts 40, 41, 42, 43, are received in bearings 46, 47, 48, 49, 50, 51, 52, 53. The bearings 46, 47, 48, 49, 50, 51, 52, 53 are formed as roller bearings, in particular tilted roller bearings, to support the high forces, which act on the crumbling shafts 40, 41, 42, 43 during crumbling of root crops.

Figure 4:
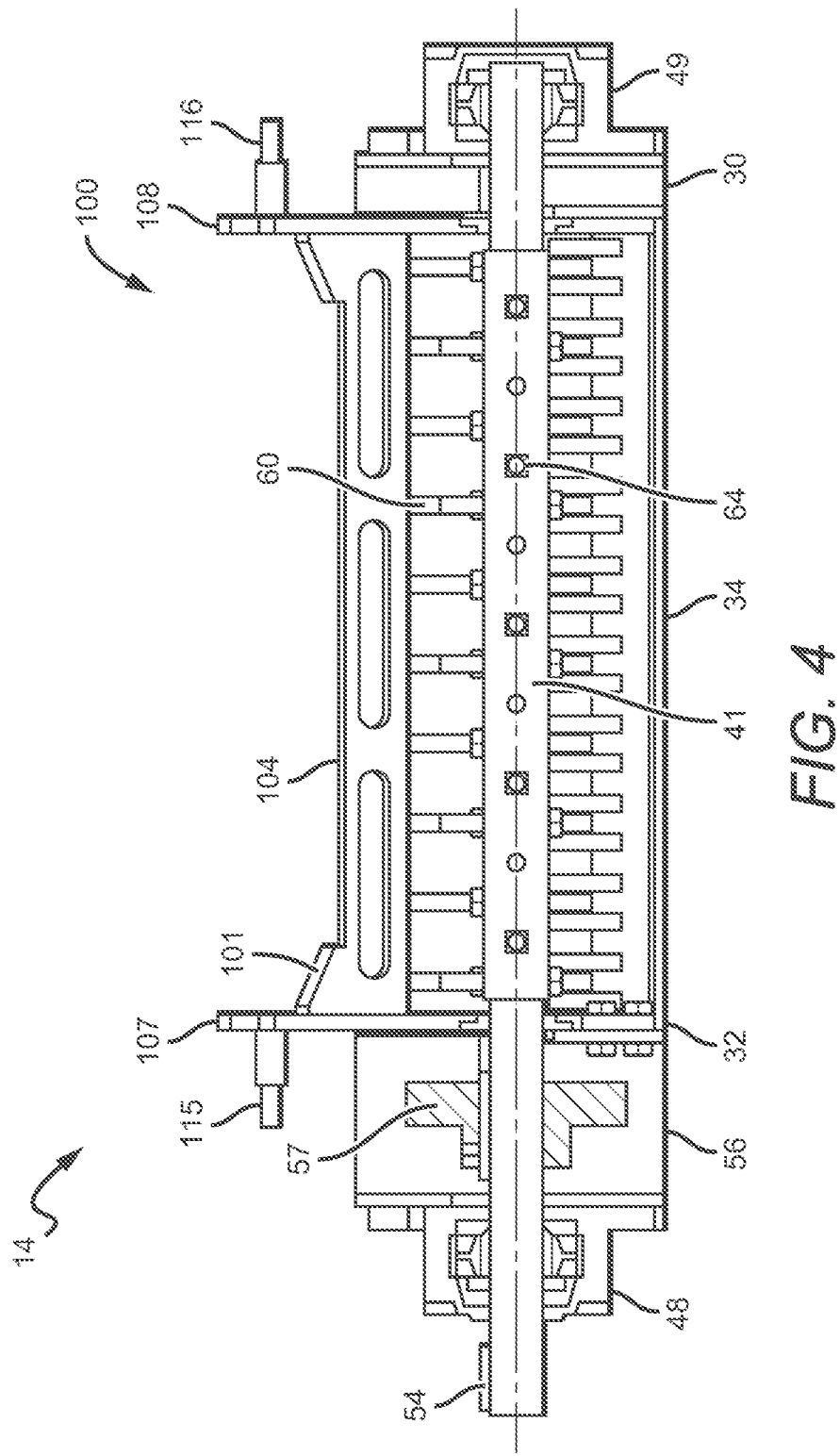
FIG. 4 is a cut through the device of FIGS. 2 and 3.

Two of the four crumbling shafts 40, 41, 42, 43 form one set, in this embodiment, the crumbling shafts 40, 41 form a first set of crumbling shafts and the crumbling shafts 42, 43 form a second set of crumbling shafts. Only one crumbling shaft 41, 43 of each set of crumbling shafts is provided with a drive shaft extension 54, 55, protruding through the respective bearing 48, 52 and engageable with a corresponding drive shaft of a drive motor or the like. Within a housing portion 33 of the second head panel 32, a gearing 56 for each set of crumbling shafts 40, 41, 42, 43 is provided, wherein gearing 56 can be seen in FIG. 4. Gearing 56 comprises a first gearing wheel 57 mounted on the crumbling shaft 41, which engages a second gearing wheel 58 fixed to crumbling shaft 40 (see FIG. 6). By engagement of the two gearing wheels 57, 58, the rotation of crumbling shaft 41 can be transferred to crumbling shaft 40 so that the crumbling shafts 40, 41 of the first set of crumbling shafts rotate at the same speed. Due to the gearing 56, they rotate in counter rotation. It shall be understood that for the second set of crumbling shafts 42, 43, an identical gearing is provided within the casing 33. In general, the two sets of crumbling shafts 40, 41, 42, 43 are formed identical and the reason for providing four crumbling shafts 40, 41, 42, 43 mainly is to increase throughput and performance of the device 14.

Figure 6:
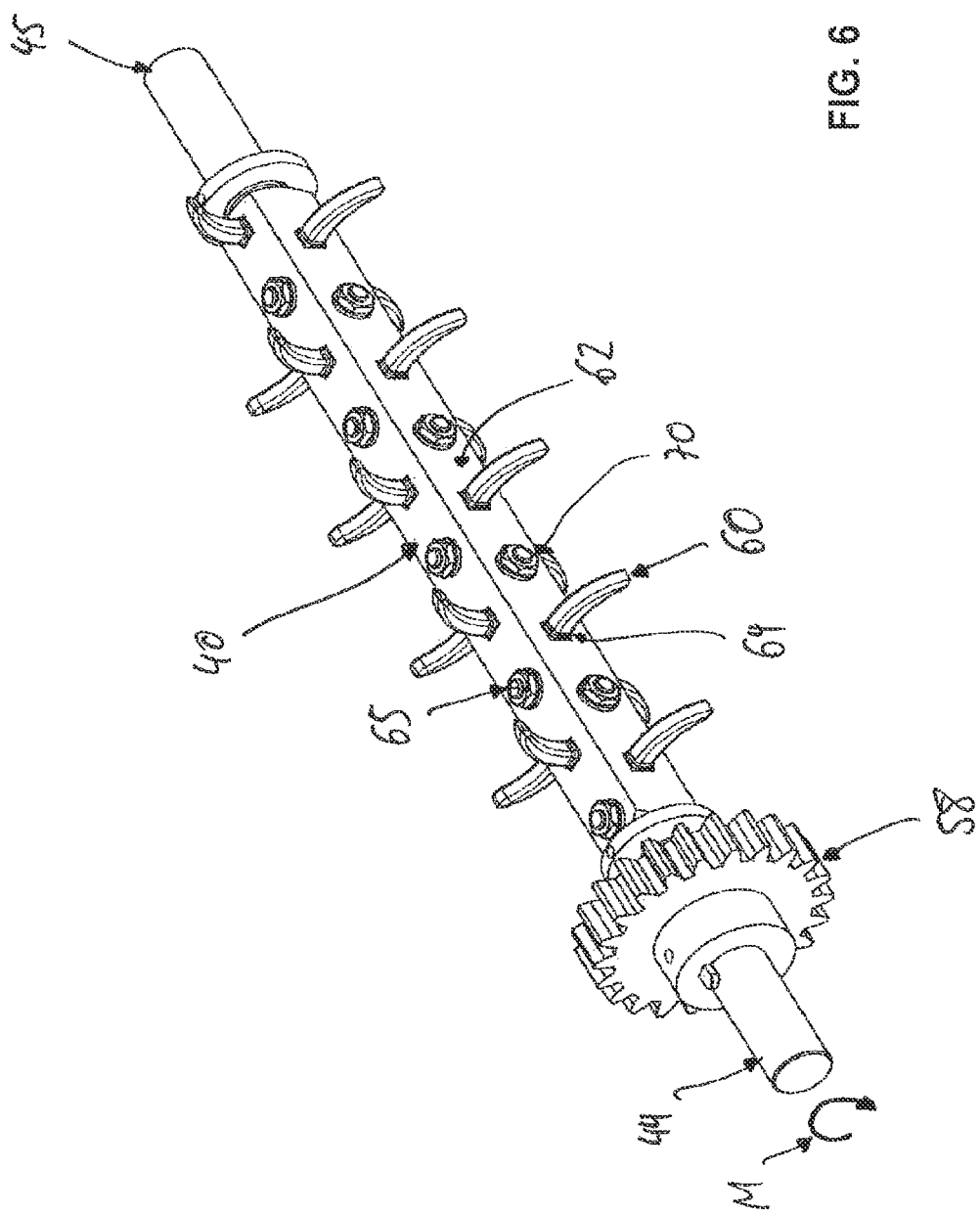
FIG. 6 is a perspective view of a crumbling shaft comprising curved hooks.

With reference to FIG. 6, the crumbling shafts 40, 41, 42, 43 (in FIG. 6, only one crumbling shaft 40 is shown; however, the design of the crumbling shafts 40, 41, 42, 43 is substantially identical) is provided with a plurality of hooks 60 (only one indicated with reference sign in FIG. 6). The hooks 60 are all formed identical to each other, however provided offset to each other and about a circumference of the crumbling shaft 40. The crumbling shaft 40 comprises a main shaft portion 62 and the two extensions 40, 42 for being received in respective bearings 46, 47. The main shaft portion 62, according to this embodiment, has a rectangular shape having four surfaces being at substantially 90° to each other. The main shaft portion 62 is provided with through bores 64, 65 (again only two in FIG. 6 indicated with reference signs), which are arranged in alternating manner through the main shaft portion 40. That is, the through bores 64, 65 alternate, while the first through bore 64 is provided in a first direction and the second through bore 65 in a second direction, which is perpendicular to the first direction of the first through bore 64. The through bores, which are parallel to each other, in embodiments of the invention are offset by a value in the range of 20 mm to 80 mm, preferably 30 mm to 50 mm and in this particular embodiment are offset by a value of 40 mm. The value may be dependent on the size of the hooks 60 and also on the type of root crop to be crumbled. 40 mm has shown to be a preferred range for sugar beets or fodder beets.

Figure 7:
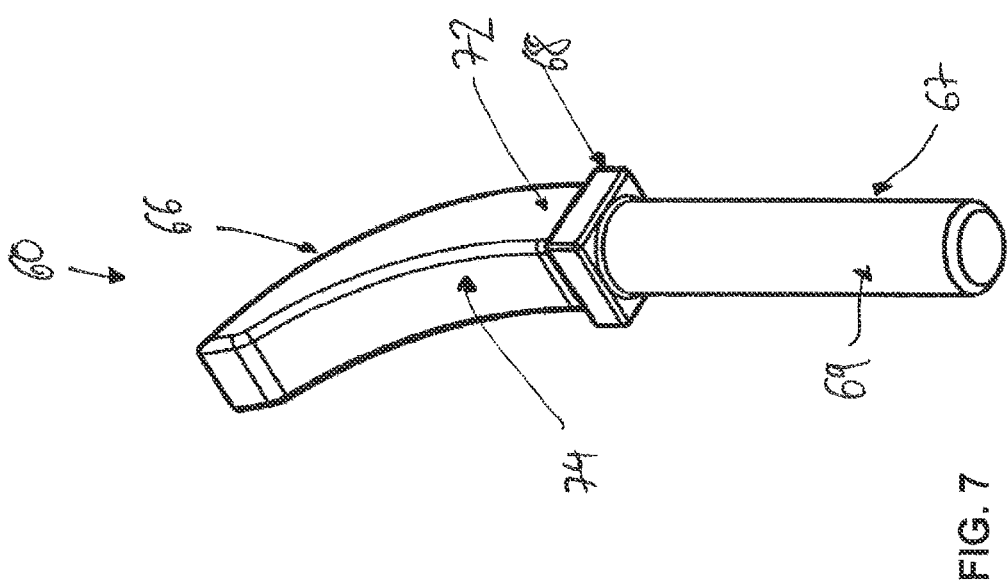
FIG. 7 is a perspective view of a hook.
Figure 9:
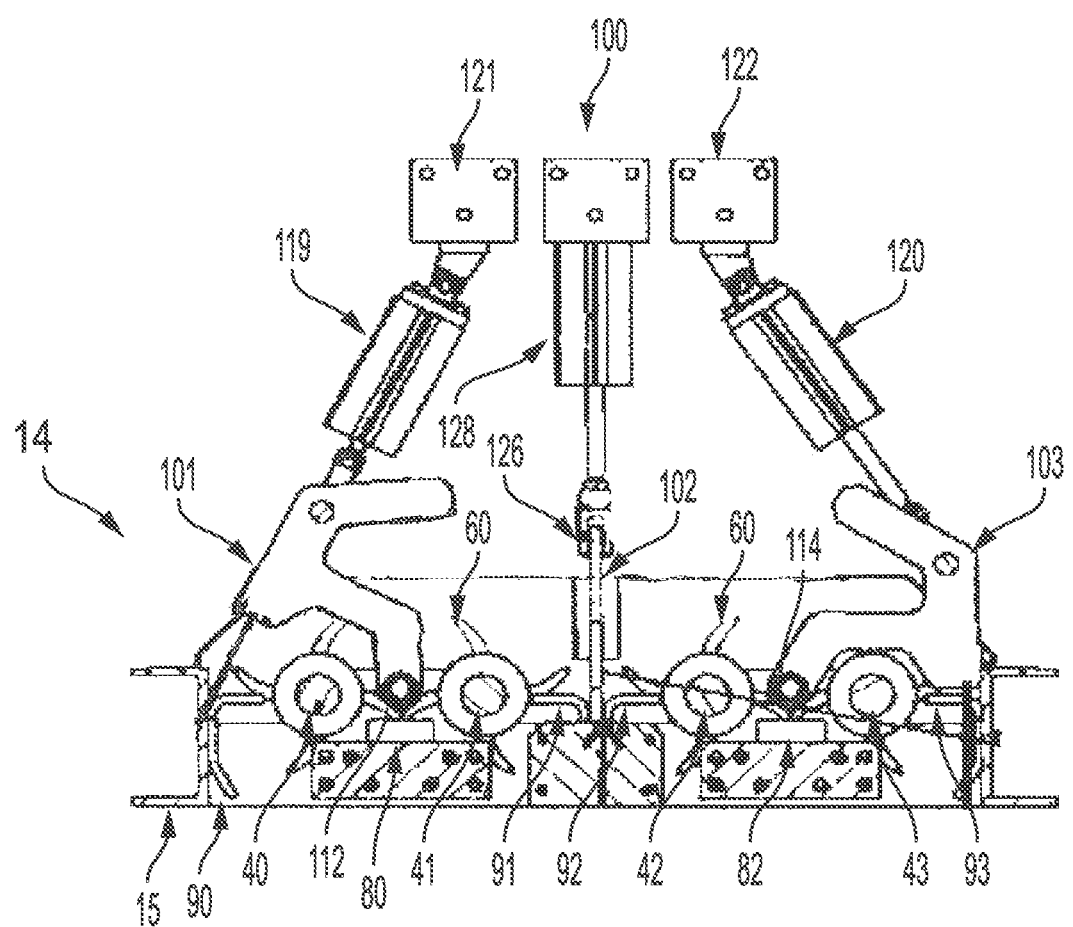
FIG. 9 is a further cut through the device for crumbling root crops.

Moreover, the hooks 60 in through bores 64, 65, which are parallel to each other, are also alternating arranged, such that they protrude alternating in opposing directions. Each hook 60 comprises a hook portion 66 (see FIGS. 7 and 8) and a mounting portion 67. Between the hook portion 66 and mounting portion 67, a flange portion 68 is provided, which serves as an abutment, when the respective hook 60 is seated in one of the through bore 64, 65. The respective hook 60 is pushed with its mounting portion 67 through the through bore 64, 65 and comes into contact with the main shaft portion 40 with its flange portion 68, such that it is in a defined position. The flange portion 68 can be designed with a square-shaped cross-section as shown in FIG. 7 or alternatively an oval cross-section. This flange portion 68 fits in a respective pressed or milled notch in crumbling shafts 40, 41, 42, 43. The mounting portion 67 is provided with a thread portion 69, which acts together with a nut 70 comprising a correspondingly provided inner threaded portion (see FIG. 6). Each hook 60 is curved into a direction of movement of the respective crumbling shaft 40, 41, 42, 43, as indicated by the moving arrow M.

Figure 8:
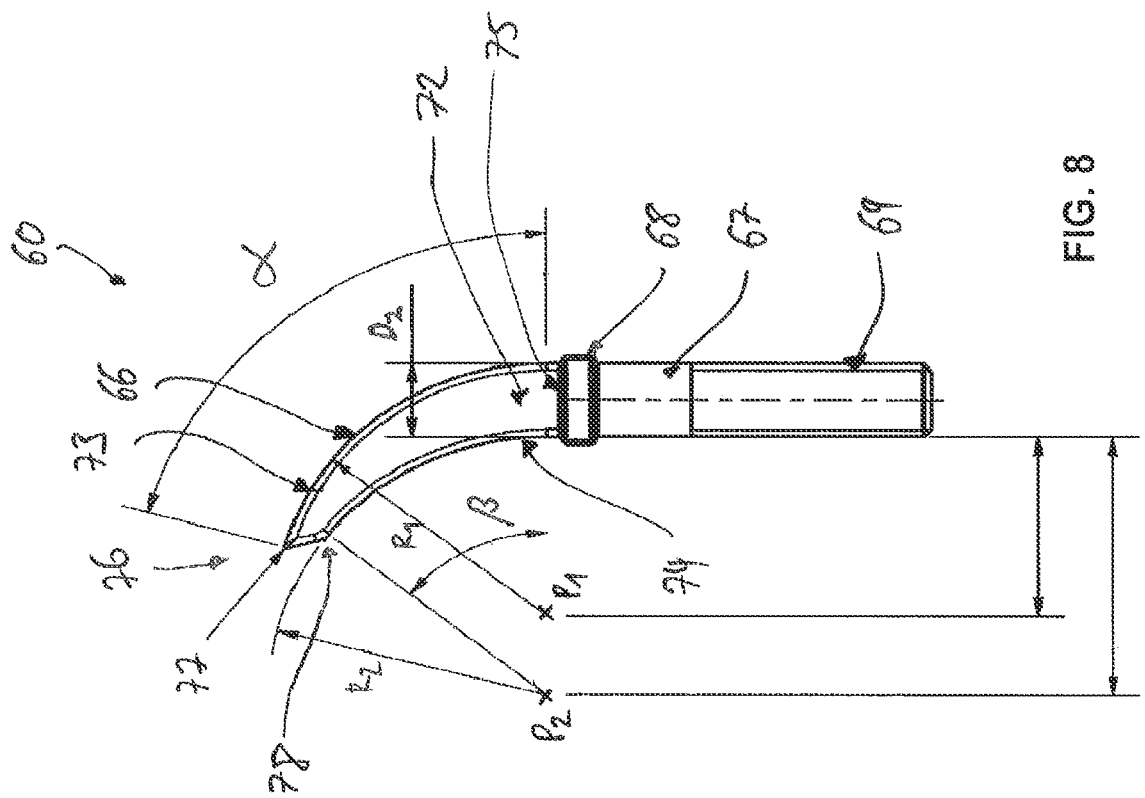
FIG. 8 is a side view of the hook of FIG. 7.

The design of the hooks is in particular shown in FIGS. 7 and 8 and will now be described. The hook portion 66 comprises a substantially rectangular cross-section with two parallel side faces 72, as well as a back surface 73 and a front surface 74. Front and back surface 73, 74 are curved and resemble a partial circle. The radius of the curvature of each of the front and back faces 73, 74 differ from each other and the radius of the front face 74 is slightly larger than the radius of curvature of the back face 73. This is not absolutely necessary, but beneficial in this embodiment. It shall, however, be understood that it could also be the other way around and that the radius of the curvature of the back face 73 is larger than the radius of curvature of the front face 74. According to this embodiment, the radius $R_1$ of the curvature of the back face is in the range of 20 mm to 40 mm, in particular in the range of 34 mm. The radius of curvature $R_2$ of the front face 74 is also in the range of 20 mm to 40 mm, in this particular embodiment in the range of 35 mm. The tapering shape of the hook portion 66 is due to an offset of the center points $P_1$, $P_2$ of each radius $R_1$, $R_2$, which are offset by the thickness $D_2$ of a base portion 75 of the hook portion 66. The thickness $D_2$ is in the range of 5 mm to 15 mm, in this particular example, it may be in the range of 10 mm. Thus, also the offset between the points $P_1$ and $P_2$ is about 10 mm, resulting in the tapering shape of the hook portion 66.

At the terminal end 76, the hook portion 66 comprises a sharp edge 77 tapering inwardly and merging via a small protrusion 78 into the front face 74. The edge portion 77 is relatively sharp and comprises a small radius, in particular in the range of 0.1 mm to 0.3 mm. Each hook 60 has a length, when measured from the edge portion 77 to the center of the base portion 75, in the range of 20 mm to 80 mm, preferably 30 mm to 50 mm, in particular about 40 mm. By this particular arrangement of the hooks 66, the edge 77 will cut into the respective root crop, when the crumbling shaft 40, 41, 42, 43 rotates and thus cause brittling, crumbling or ripping off portions of the root crop due to the tapering or wedge shape of the hook 60. When measured in angles α and β of the extension of the partial circular portions formed by the back face 73 and front face 74, the extension of angle α is in the range of 45° to 90°, in particular in the range of 60° to 80°, more preferred about 75°. Similarly, the extension of the angle β is shorter to provide the wedge portion at the edge 77 and is in the range of 30° to 80°, in particular 40° to 60° and more preferred in the range of 50°.

Figure 3:
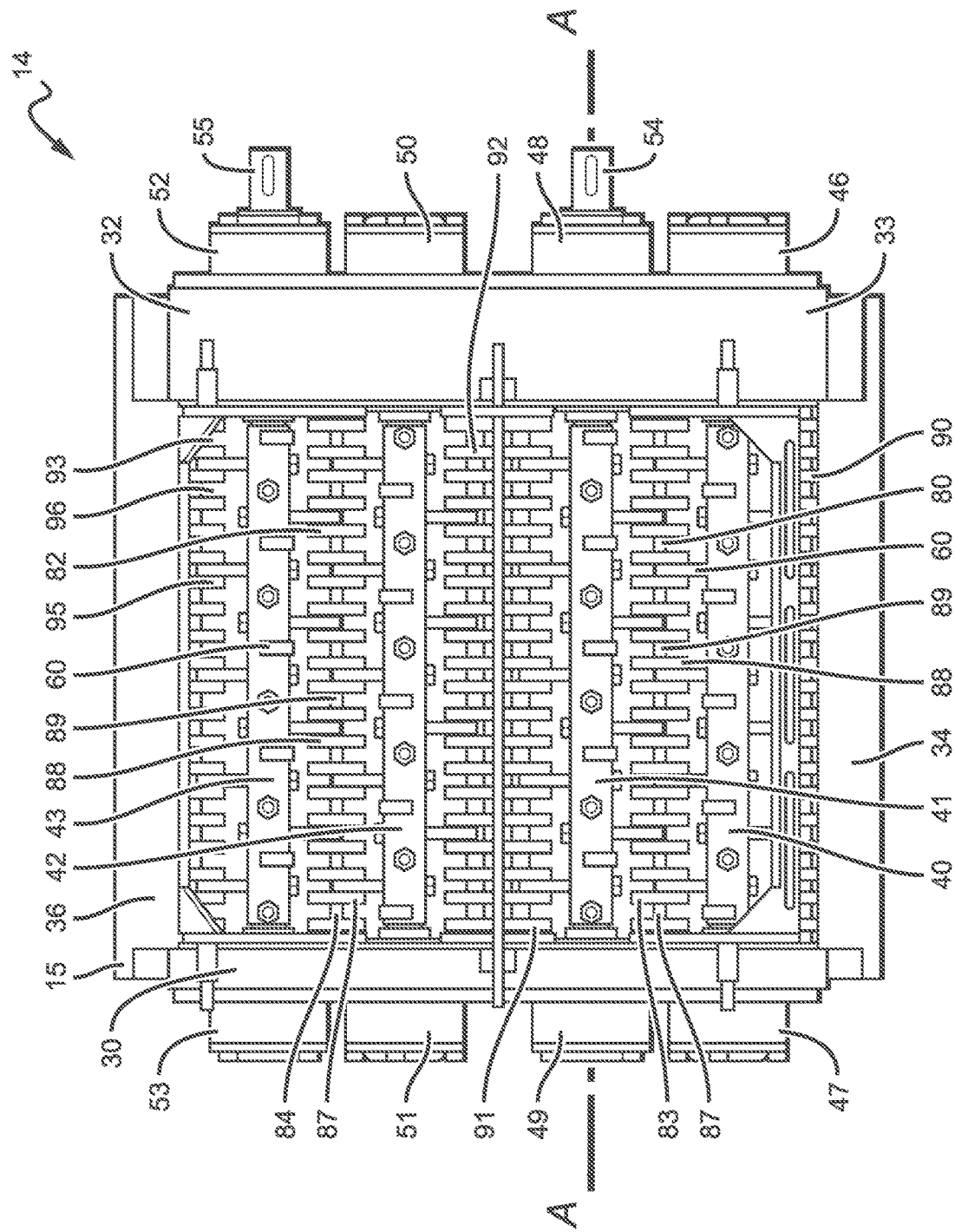
FIG. 3 is a top view of the device of FIG. 2.

Now, again turning back to FIGS. 2 to 5, when the crumbling shafts 40, 41, 42, 43 rotate, in particular in a counter rotation movement, they require a counterpart for supporting the root crops to be cut. This counterpart is formed by a cutting rake 80, 82, wherein one cutting rake 80, 82 is provided for each of the first set of crumbling shafts 40, 42 and the second set of crumbling shafts 42, 43. Each cutting rake 80, 82 is formed the same and comprises a longitudinal bar 83, 84 extending from the head portion 30 to head portion 32 and attached thereto, by means of a respective mounting plate 85, 86 (see FIG. 5). By means of these mounting plates 85, 86, the cutting rake 80, 82 is attached to the main frame 15. The cutting rake 80, 82 comprises a plurality of metal plates 87 attached to the bars 80, 82, respectively, and offset in axial direction to each other, such that they form protrusions 88 and recesses 89 for cooperating with the hooks 60 on the respective crumbling shafts 40, 41, 42, 43. The protrusions and recesses 88, 89 are provided for interlaced movement with the hooks 66 and provide a counter support or counter blade for the root crops to be cut. Additionally, the protrusions and recesses 88, 89 provide a sieving function, which might be inferred from e.g. FIGS. 3 and 5 and serves such that root crop pieces, which are larger than a specific size, are not able to pass to the outlet side 22.

By means of the mounting plates 85, 86, the vertical height of the cutting rakes 80, 82 (see FIG. 5) is adjustable. While the cutting rakes 80, 82 are shown in an intermediate position in FIG. 5, they might be mounted further upwards, such that the size of the crumbling root crop pieces becomes smaller, and might also be attached to a lower portion of main frame 15, such that bigger pieces of root crops are cut from the root crops. However, in an upward direction, the position is limited by the cutting circle C, which is a circle connecting the moving point of the edges 77 of the hooks. The bar 83, 84 is not able to move further upward, otherwise a contact between the edges 77 and the bar 83, 84 would occur.

Figure 5:
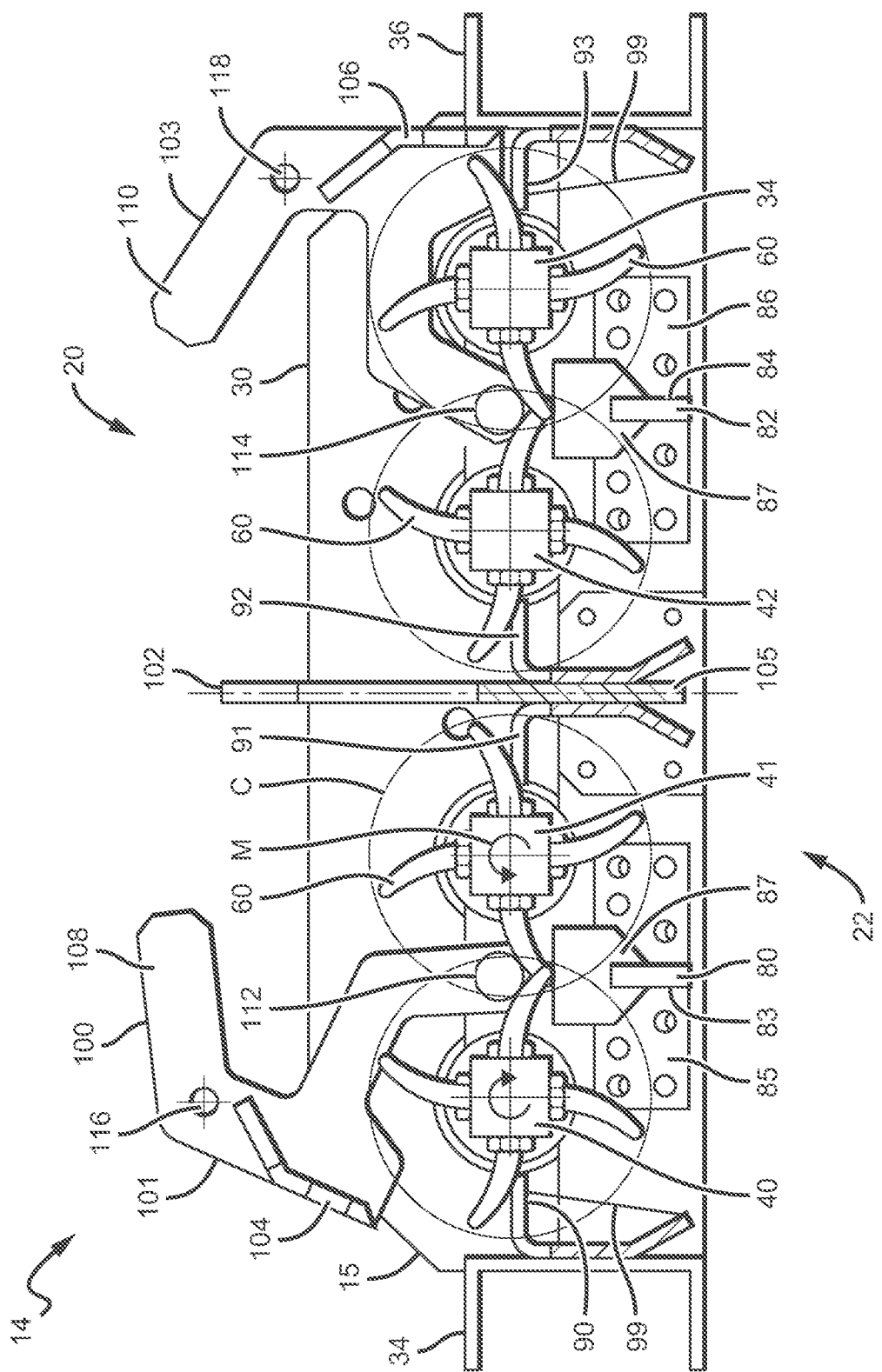
FIG. 5 is a further cut through the device of FIGS. 2 and 3.

Additionally to the cutting rakes 80, 82, two cleaning rakes 90, 91, 92, 93 are provided for each of the first set of crumbling shafts 40, 41 and second set of crumbling shafts 42, 43. The cleaning rakes 90, 91, 92, 93 extend along the crumbling shafts 40, 41, 42, 43 and parallel to them. They are formed as a counterpart to the cutting rakes 80, 82. The cleaning rakes 90, 91, 92, 93 are attached to either the head portions 30, 32, or the side panels 34, 36 of the main frame 15. They might be adjustable in height position, even though this is not particularly necessary for the present invention. They are used to clean off stuck or adhered root crop pieces from the hooks 60 respectively, when the hooks 60 move upwards. Thus, they avoid that uncut pieces of the root crops are moved from the inlet side 20 to the outlet side 22. Since the cleaning rakes 90, 91, 92, 93 do not have to be very high forces; they are made out of a sheet metal, in particular punched out of a sheet metal and bend, such that they have a substantially angled shape. Again, protrusions 95 and recesses 96 are formed at the cleaning rake 90, 91, 92, 93 by punching, for interlaced movement with the hooks 60, when the crumbling shafts 40, 41, 42, 43 rotate. In a preferred embodiment the cleaning rakes 90, 91, 92, 93 are stabilized by gusset plates 99 fixed by welding as indicated in FIG. 5.

For the event that one or more of the root crops to be crumbled get stuck or clogged and do not move anymore, the device 14 of the present invention comprises a de-clogging device 100. This de-clogging device will now be described with reference to FIGS. 2, 5, 9, 10 and 11 in particular. The de-clogging device 100 is operable for de-clogging clogged root crops from the cutting rake 80, 82 or cleaning rakes 90, 91, 92, 93. According to this particular embodiment, in which the device 14 comprises the two sets of crumbling shafts 40, 41, 42, 43, the de-clogging device 100 comprises three de-clogging elements 101, 102, 103, while the second de-clogging element 102 is used for both sets of crumbling shafts 40, 41, 42, 43. The first and third de-clogging elements 101, 103 are substantially formed identical to each other, but arranged mirrored and opposite to each other. Each of the de-clogging elements 101,102, 103 is arranged to be movable adjacent to a cleaning rake 90, 91, 92, 93. There might be additional de-clogging elements for de-clogging root crops which are clogged to the cutting rake 80, 82, however, it is shown that this is more seldom and mainly root crops get clogged at either the connecting portion between the first and second sets of crumbling shafts 40, 41, 42, 43, or side portions, that is at the side panels 34, 36. Root crops have more tendencies to be clogged at the cleaning rakes 90, 91, 92, 93, since there is less cutting action than at the cutting rakes 80, 82. For a complete cutting of all root crops provided to the inlet side 20, it is necessary that the root crops are able to "dance" on the crumbling shafts 40, 41, 42, 43. If too many root crops are loaded into the hopper 13, it might happen that the root crops are pressed towards the rakes 80, 82, 90, 91, 92, 93 and thus become clogged.

According to the present embodiment, the de-clogging element 102 is at a central portion and the de-clogging elements 101, 103 are at the side panels 34, 36. Each of the de-clogging elements 101, 102, 103 comprise a bar 104, 105, 106 with a longitudinal extension parallel to said crumbling shafts 40, 41, 42, 43 and movable upwardly for raising clogged root crops or root crop pieces.

The outer de-clogging elements 101, 103 comprise respective brackets 107, 108, 109, 110, between which the bar 104, 106 extends and to which the bar 104, 106 is attached to. The brackets 107, 108, 109, 110 are pivotally attached to the head portions 30, 32 via respective pivot hinges 111, 112, 113, 114, which are substantially arranged vertically above the cutting rakes 80, 82, respectively. They might also be positioned at other positions within the scope of the invention.

At the brackets 107, 108, 109, 110, moreover, engagement pins 115, 116, 117, 118 are attached, extending outwardly away from the respective bracket 107, 108, 109, 110. The engagement pins 115, 116, 117, 118 are provided for an engagement with an activation piston 119, 120 (see FIG. 9). The activation piston 119, 120 is attached to a fixing portion 121, 122 and is able to contract with respect to the right-hand side of FIG. 9 (piston 120) to a position as shown in the left-hand side of FIG. 9 (piston 119). When the pistons 119, 120 retract, the de-clogging element 101, 103 is pivoted about the pivot hinges 111, 112, 113, 114 and thus, the bar 104, 106 is raised in an arch-shaped path starting from the respective cleaning rake 90, 93 and upwardly towards the centre of the device 14 and thus, in a direction of the rotating direction of the crumbling shafts 40, 43. The bars 104, 106 are moreover provided with respective through holes 124 (only shown with reference sign in FIG. 11) thus, increasing a friction between the clogged root crop and the bar 104, such that the clogged root crop might be transported towards a central direction and thus again engaged by means of the hooks 60.

The central de-clogging element 102 acts in a similar manner. It comprises engagement portions 125, 126 (see FIG. 10), which are engaged by a third pair of pistons 128 (only one shown in FIG. 9; it shall be understood there is a second one for engagement section 125 on the opposite side of the device). These pistons 128 can be activated in a parallel manner, such that the whole de-clogging element 102 is straightly lifted upwards, but they might also be activated in sequence, such that the de-clogging element 102 is pivoted and in a first step, portion 125 is raised and lowered again and in a second step, portion 126 is raised and lowered again. This also leads to the effect that clogged root crops are pushed towards the centre of the device 14.

Figure 12:
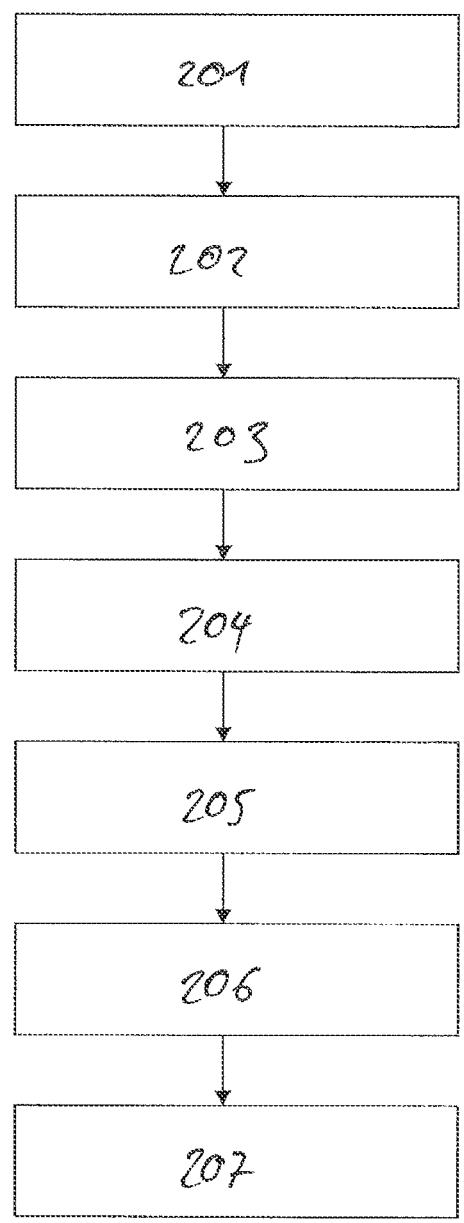
FIG. 12 is a flowchart of a method for determining components in root crops.

FIG. 12 illustrates a method 200 for determining components in root crops. A method according to this particularly preferred embodiment comprises seven steps in the following order:

The method starts with the step of crumbling 201 the root crops into substantially equal sized fine pieces using the device 14, as described beforehand. Thus, the root crops are fed into the hopper 13, the crumbling shafts 40, 41, 42, 43 are activated to rotate and root crop pieces are provided at the outlet side 22. Preferably, the crumbling shafts are rotated at a speed of about 300 to 1000 rpm, wherein a higher rotational speed results in smaller pieces of root crop and a lower rotational speed results in bigger pieces of root crop.

In the second step 202, a stream of fine pieces of root crop 24 is generated and the fine pieces of root crop are transported with the aid of a transporting device 5. Afterwards, by means of the roller 6 in particular, a step of homogenizing 203 or evenly distributing the fine pieces of root crop 24 in the stream is carried out. Then, an irradiating step 204 of the stream of fine pieces of root crop with light in the near infrared range is carried out and the reflected or absorbed radiation is recorded 205. This recorded radiation is converted 206 into a spectral signal, and processing 207 of the spectral signal for determination of the components is carried out.

The invention claimed is:

1. A device for crumbling root crops, preferably into substantially equal sized pieces, comprising:
a main frame having an inlet side and an outlet side;
a hopper at the inlet side of the main frame for collecting root crops;
at least one crumbling shaft rotatable supported in the main frame, the crumbling shaft being provided with a plurality of curved hooks comprising a sharp edge, preferably curved into a direction of rotation of the crumbling shaft;
a non-rotating cutting rake having a plurality of protrusions and recesses arranged for interlaced movement with the hooks;
a de-clogging device for de-clogging clogged root crops from the cutting rake; and
a cleaning rake adjacent to or opposite the cutting rake for stripping off root crop pieces from the hooks,
wherein the cutting rake is adjustable in height for adjusting a vertical distance to said crumbling shaft.

2. The device of claim 1, wherein a back face of the curved hooks is curved about an angle of 30° to 90° from a base portion of the hook to a terminal end of the hook.

3. The device of claim 1, wherein the curved hooks are displaced to each other provided about the circumference of the crumbling shaft.

4. The device of claim 1, wherein the curved hooks have a length in a range of 20 mm to 80 mm, measured along a center line of the hooks.

5. The device of claim 1, wherein the curved hooks have a cross section in a range of 100 $mm^2$, measured at a foot portion and/or in a middle portion of the hooks.

6. The device of claim 1, wherein the curved hooks are axially offset to each other by a value in the range of 10 mm to 100 mm.

7. The device of claim 1, wherein the curved hooks are removably fixed to the crumbling shaft.

8. The device of claim 1, wherein the de-clogging device comprises a first de-clogging element for the cutting rake.

9. The device of claim 8, wherein the first de-clogging element is in the form of a bar with a longitudinal extension parallel to said crumbling shaft and movable upwardly for raising clogged root crops or root crop pieces.

10. The device of claim 8, wherein the de-clogging device comprises a second de-clogging element for the cleaning rake.

11. The device of claim 10, wherein the second de-clogging element is in the form of a bar with a longitudinal extension parallel to said crumbling shaft and movable upwardly for raising clogged root crops or root crop pieces.

12. The device of claim 8, wherein the first de-clogging element is connected to a drive for intermittently driving the first de-clogging element.

13. The device of claim 10, wherein the second de-clogging elements is connected to a drive for intermittently driving the second de-clogging element.

14. The device of claim 1, comprising a set of first and second crumbling shafts supported in said frame, which are arranged for counter-rotating, wherein one rake is provided between the shafts having opposingly arranged protrusions and recesses.

15. The device of claim 14, comprising a second set of third and fourth crumbling shafts.

16. A device for determining components in root crops, comprising:
the device for crumbling root crops according to claim 1 for providing a stream of root crop crumbles;
a transport device for transporting the stream of root crop crumbles;
an equalizing roller for homogenizing the stream of root crop crumbles; and
a measuring device for identification and quantification of ingredients.

17. The device of claim 16, wherein a support is provided below the transport device for supporting the pressure of the roller.

18. A method for crumbling root crops into substantially equal sized pieces, comprising:
crumbling the root crops into substantially equal sized fine pieces using a device according to claim 1.

19. A method for determining components in root crops, comprising the following sequence of steps:
crumbling the root crops into substantially equal sized fine pieces using a device according to claim 1;
generating a stream of fine pieces of root crop, and transporting the fine pieces of root crop with the aid of a transport device;
homogenizing or evenly distributing the fine pieces of root crop in the stream;

irradiating the stream of fine pieces of root crop with light of the near infrared range;
recording the reflected and/or absorbed radiation;
converting radiation into a spectral signal; and
processing of the spectral signal for determination of the components.

20. The method of claim 19, comprising:
evenly supplying the root crops to the device for crumbling root crops, such that the root crops are free to move and spring on the cutting shafts.

* * * * *